United States Patent [19]

Pegg et al.

[11] Patent Number: 5,436,147
[45] Date of Patent: * Jul. 25, 1995

[54] HETEROBIFUNCTIONAL CROSSLINKED AGENTS FOR IMMOBILIZING MOLECULES ON PLASTIC SUBSTRATES

[75] Inventors: Randall K. Pegg, Amelia Island; Mary S. Saunders, Monticello, both of Fla.

[73] Assignee: Nucleic Assays Corporation, Amelia Island, Fla.

[ * ] Notice: The portion of the term of this patent subsequent to Jan. 18, 2011 has been disclaimed.

[21] Appl. No.: 78,753
[22] Filed: Jun. 16, 1993

Related U.S. Application Data

[63] Continuation-in-part of Ser. No. 663,120, Mar. 1, 1991, Pat. No. 5,279,955.
[51] Int. Cl.⁶ ............... C12N 11/06; G01N 33/549; C07C 69/34
[52] U.S. Cl. .................. 435/181; 435/7.92; 436/532; 530/816; 560/190
[58] Field of Search .......... 435/7.92, 181; 436/532; 530/816; 560/190

[56] References Cited

U.S. PATENT DOCUMENTS

| | | | |
|---|---|---|---|
| 4,229,537 | 10/1980 | Hodging et al. | 435/180 X |
| 4,657,873 | 6/1987 | Gadow et al. | 436/532 |
| 4,808,530 | 2/1989 | Means et al. | 430/180 |
| 4,889,916 | 12/1989 | Packard et al. | 435/181 X |
| 5,002,883 | 3/1991 | Bieniarez et al. | 435/181 X |

FOREIGN PATENT DOCUMENTS

2184127 6/1987 United Kingdom .

*Primary Examiner*—David M. Naff
*Attorney, Agent, or Firm*—R. Kevin Pegg

[57] ABSTRACT

Heterobifunctional crosslinking agents are synthesized that covalently link molecules such as enzymes, cells, proteins and nucleic acids to a plastic substrate. The agents contain a central ring structure having a hydrophobic hydrocarbon chain that binds to a plastic substrate and distal to the hydrophobic chain one or more hydrophilic chains terminating in a reactive group that covalently binds the molecule. Immobilized molecules are useful in diagnostic assays or bioreactors. Preferred heterobifunctional crosslinking agents have the following structures:

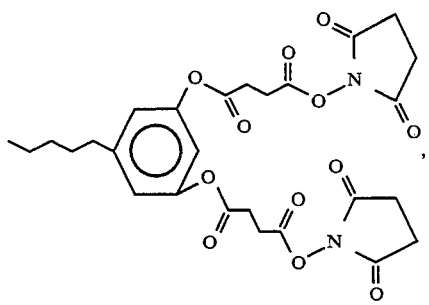

,

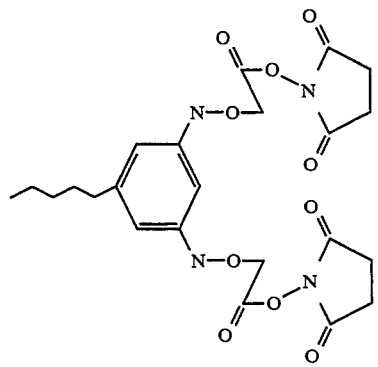

and

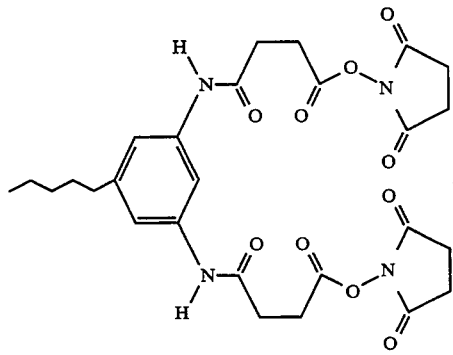

5 Claims, 3 Drawing Sheets $R_1$: $CH_3-(CH_2)_n-$ $R_2$: $-O-$ ; $-NH-$ ; $-NOH-$ ; $-SH-$ ; $-CH_2-$ $R_3$:

$R_4$: H ; $SO_3$

HETEROBIFUNCTIONAL CROSSLINKED AGENTS FOR IMMOBILIZING MOLECULES ON PLASTIC SUBSTRATES

This application is a continuation-in-part of application Ser. No. 07/663,120, filed Mar. 1, 1991, now U.S. Pat. No. 5,279,955.

BACKGROUND OF THE INVENTION

1. Field of the Invention

This invention relates to a novel heterobifunctional composition useful in immobilizing reagents on plastic surfaces. More specifically this invention comprises a molecule with hydrophobic regions that can intercalate into plastic and hydrophobic reactive groups that can covalently attach to other molecules. When contacted with plastic these novel reagents can, in a single rapid step, produce a reactive surface capable of binding other reagents.

2. Background Information

The practice of biotechnology, and particularly diagnostics, has increased the demand for products requiring immobilized reagents. "Reagents" includes proteins, nucleic acids, cells, drugs, and small molecule haptens. Substrates are insoluble matrices for immobilzation and can be plastic, glass, silica, carbon, cellulose, or other materials. Plastics are particularly useful substrates as they can be formed into a variety of shapes such as cups, discs, dipsticks, spheres, fibers, tubes, membranes, and particles. Plastics are used as stirface coats. Additionally, plastics have a high degree of biocompatability, and may be produced of materials having excellent optical properties. Typical plastics useful as substrates include polypropylene, polystyrene, polyethylene, polyvinyl chloride, polysulfone, polycarbonate, cellulose acetate and others. Plastics of styrene, vinyl chloride and carbonate are widely used when optical properties are a consideration.

Plastics are often used directly as substrates for direct immobilization of macromolecules. Polystyrene and polyvinyl chloride will anchor large molecules by electrostatic attraction. However, small molecules require attachment to larger "carrier" molecules before being bound to the plastic. Also, poor binding to most plastics limits the use of adsorption immoblization to high surface area systems. For instance, polystyrene latex particles can immobilize far more protein molecules per gram of plastic than molded polystyrene products.

Modification of the plastic surface has been used to increase the electrostatic interaction and increase the binding of some reagents. Electrostatic interactions alone will immobilize only a limited number of reagents, and detergents introduced in the system can cause reagent loss.

Reagent molecules are typically immobilized on a substrate by way of a linker molecule. Homobifuctional and heterobifunctional compounds have been devised to link a group present on the reagent to a group present on the substrate. As examples, disuccimidyl suberate and glutaraldehyde are homobifunctional compounds that can covalently bridge an amine group on a reagent molecule to an amine group present on a substrate, such as aminopolystyrene. Additionally, some plastics, such as methyl methacrylate and polyethylvinylacetate, have been developed to bear hydroxyls that can be convened to reactive intermediates. Reactive groups that can be provided include epoxides, hydroxysuccinimide esters, aldehydes, nitrophenyl chloroformate, activated thioIs, trityl, tresyl chloride, or other means for reacting free amines, hydroxides or sulfhydryls.

Reagents can also be hydrophilic pigments. In some industries the application of an inert topcoat to plastic substrates is needed for coloring or improved wear characteristics.

Modifications of the plastic surfaces to bear amines, hydroxyls, and sulfhydryls that can be crosslinked or otherwise modified often results in undesirable characteristics, particularly opacity or decrease structural integrity.

One system that has become available involves incorporation of a methyl imine function. This product requires the end user to convert the methyl imine functionality to a reactive group by addition of crosslinkers (NUNC, Naperville, Ill.). Another system treats plastic with a copolymer of phenylalanine and lysine amino acids to provide a support for a crosslinker (U.S. Pat. No. 4,657,873; Gadow, et al.). Gadow et al. is typical of the other prior attempts at forming reactive surfaces in that binding of a reagent requires several steps and usually entails crosslinking a nucleophile on the reagent molecule with a nucleophile on the plate.

Bienarz et al. (U.S. Pat. No. 5,002,883) also uses an amine bearing surface in combination with a "bridging" molecule to crosslink a reagent molecule to a plastic surface. As does Tetsuo et al. (UK Patent number GB2184 127A) which specifically requires hydrophilic functional groups on the surface prior to forming a bond between the reagent and the surface. Packard et al. (U.S. Pat. No. 4,889,916) has a similar requirement for two functional groups to be crosslinked, however, in the case of Packard the reaction is between sulfhydryl groups on both the substrate and the reagent molecule.

The technology of means et al. (U.S. Pat. No. 4,808,530) produces reagent bearing surfaces by convening hydrophilic groups on proteins to hydrophobic moieties. When the derivatized proteins are contacted to unmodified plastics the protein is bound by nonspecific adsorption to the surface.

All of the above technologies require a plurality of steps to modify the surface and then crosslink the reagent molecule of interest, or as in the case of Means et al., to modify the protein itself for attachment. Bieniarz et al. describe their derivatization process as requiring several steps over several hours. Typical procedures involve a one hour pretreatment of a prederivatized aminopolystyrene bead, followed by one hour derivatization with several clean up steps, the final step of adding reagent member required overnight incubation. Likewise, Gadow et al. describes a first derivatization step involving heating and mixing, followed by agitation for 30 minutes at room temperature, followed by a 24 hour incubation. At this stage the technology still is incapable of protein binding. The treated plastic resin must be activated for an additional 30 minutes with glutaraldehyde, the actual crosslinking reagent, and washed prior to protein binding.

Means et al. stipulates protein modification prior to binding to a surface. The proteins were modified and purified over the course of several hours, and plastic surfaces were contacted with the protein for an additional several hours. Packard et al. describes labeling of protein species using a heterofunctional crosslinker. As in Means et al. the Packard technology involves several steps to modify a protein surface, again requiring several hours and extensive purification.

Tetsuo et al. specifies modifying both the protein and the plastic surface. Introduction of thiol groups into proteins required 1 hour plus gel filtration cleanup. Activation of a plastic support required several sequential steps over several hours, plus removal of the reactants. Immobilization of derivatized protein required an additional 24 hours plus cleanup.

Clearly, there is a need for a simple rapid agent tbr producing activated surfaces capable of binding reagents. In this application we describe a chemical agent capable of producing an activated surface in only a single step. The activated surface is then capable of binding an unmodified reagent without any additional process steps.

SUMMARY OF THE INVENTION

The invention comprises a heterobifunctional molecule and plastic substrate to covalently immobilize a reagent. Substrates are articles of plastic and may be formed into beads, rods, cups, membranes, or tubes. Substrates may be of polymers of vinyl, ethylene, propylene, sulfone, carbonate, or a combination thereof. The heterobifunctional molecule comprises a molecule having three distinct regions. More specifically the molecule has a central ring structure and two functional groups at opposite positions. One functional region is a hydrocarbon "tail" or chain of three or more ethyl groups terminating in a methyl function. A second region joins at the ring position distal to the hydrocarbon tail and comprises one or more hydrophilic chains terminating in a reactive functional moiety. The reactive groups join the central ring at points that are hydrophilic in nature. This feature aids in the orientation of this molecule, highly hydrophobic on one end, wettable on the opposite end.

Reactive groups are those molecules that can react with a group on the reagent member for immobilization. Reactive groups include, but are not limited to: hydroxy succinimide, nitrophenyl chloroformate, activated (reduced) thiol, trityl, tresyl chloride, acid halides, epoxides, diazo, or any other reactive group.

An important feature is the diverse types of assays that can be performed using this invention including, but not limited to: immunoassay for diagnosis involving colorimetric, fluorometric and radiometric means; affinity assays chromatography; ligand mediated analysis; and facilitated cell adhesion studies. The invention could be used to produce immobilized cell and enzyme bioreactors or as a novel adhesive and surface modifying agent.

Another important aspect of this invention is the ability to form an activated surface in a single step. After a brief (less than 5 minutes in most cases) contact with the activating molecule the surface is capable of binding reagent molecules.

BRIEF DESCRIPTION FO THE DRAWING

FIG. 1 depicts the design of the heterobifunctional agent. R1 illustrates the hydrocarbon tail. R2 illustrates the hydrophilic appendages bridging the reactive groups with the hydrophobic regions. R3 demonstrates some of the types of reactive groups that can be substituted.

DETAILED DESCRIPTIon OF THE INVENTION

Figure 1:
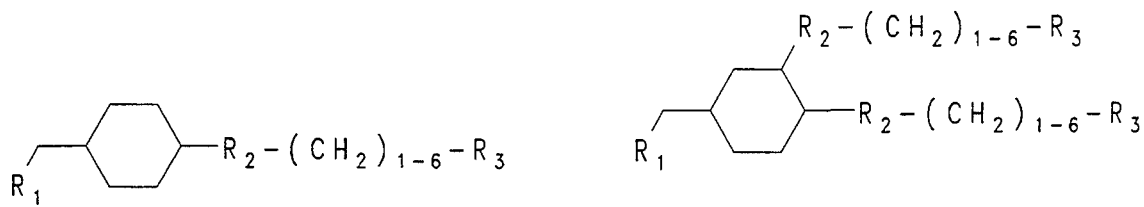
Figure 1:
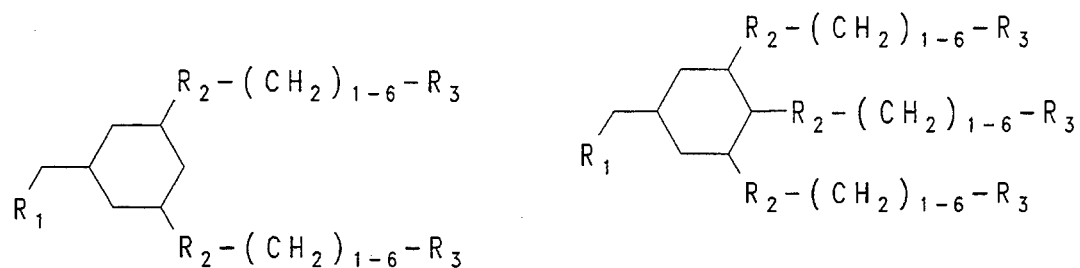
Figure 1:
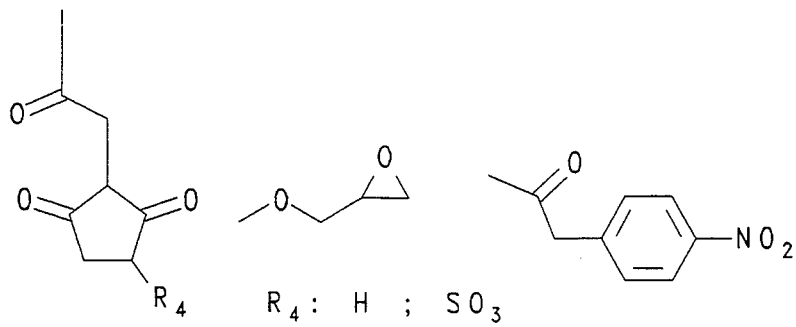
Figure 1:
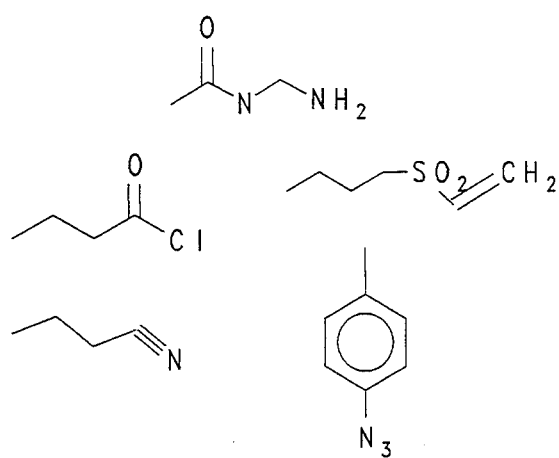

The invention for immobilizing reagents comprises: a substrate; a heterobifunctional molecule having a hydrophobic tail attached to a central ring, and, in a separate structure on the ring opposite from the hydrophobic tail, a hydrophilic region with a reactive group; and a reagent molecule capable of covalently attaching to the reactive group.

In a preferred embodiment the hydrophobic tail comprises at least two ethyl groups terminating in a methyl group; the hydrophobic tail capable of intercalating the plastic substrate thereby anchoring the molecule and orientating the reactive moieties. In a preferred embodiment the second functional region comprises one or more hydrophilic chains terminating in a reactive functional moiety joined at the ring position distal to the hydrocarbon tail. In a further embodiment the point at which the reactive groups are bound to the ring is a hydrophilic bond such as an amine, hydroxyl, imine, hydroxylamine, carboxylic acid or other group. It is an embodiment of this invention that when an aqueous solution of the reagent is applied the association of the hydrophobic region with the substrate is essentially irreversible and reactive groups extend into the solution to react with the reagent molecules.

A particularly unique embodiment of this invention is the ability of the heterobifunctional molecules described herein to form an activated surface in a single step. One need only contact the reagent to the plastic to have an activated surface capable of immobilizing a second reagent molecule. It is a particularly preferred embodiment that this activating step can be performed in only five minutes or less.

In a particularly preferred embodiment the heterobifunctional molecule is derived from reacting succinic anhydride to 5-pentyl resorcinol. The carboxylic acid groups thus obtained are then condensed with N-hydroxy-succinimide to produce reactive esters.

In a preferred embodiment the hydrophilic linkers on the central ring structure may be moieties derived from hydroxyls, amine or imines. In still another embodiment of this invention the linking groups between the hydrophilic ring moieties and the reagent binding groups may be from 1 to 6 carbons. In still another embodiment the reactive reagent binding groups may be N-hydroxy succinimide, sulfo-n-hydroxy succinimide or thionyl chloride.

The types of molecules that can be immobilized to the plastic by this molecule include, but are not limited to: enzymes; antibodies, both monoclonal and polyclonal; cellular proteins; nucleic acids, DNA, RNA and oligonucleotides; drugs; and xenobiotics.

Preferred substrates are plastics derived from polymers of vinyl, ethylene, propylene, sulfone, carbonate, or a combination thereof. In a preferred embodiment the plastic substrate is a molded article, a coating, a pellicular or porous bead, or a porous sheet such as a membrane. In a particularly preferred embodiment the substrate is polystyrene formed in the shape of a microtiter well.

A preferred embodiment is a plastic substrate of optically clear polystyrene formed into the shape of a disposable cuvet for spectrophotometric assay. In another preferred embodiment the plastic surface is formed into a dipstick for ease in pertbrining assays.

Reagent members comprise protein, nucleic acid, hapten or cell materials. Proteins are the preferred embodiment, in a particularly preferred embodiment the immobilzed protein is an antibody directed against an analyte to be measured in an assay. "Assays" in these embodiments comprise analysis of drugs, haptens, proteins, nucleic acids cells, or other molecules relevant to diagnosis. A full description of immunoassay methods and analytes are described in Tijssen, *PRACTICE AND THEORY OF ENZYME IMMUNOASSAYS, LABORATORY TECHNIQUES IN BIOCHEMISTRY AND MOLECULAR BIOLOGY* (1985), herein incorporated by reference.

In still another embodiment the reagent member bound to the reactive groups of the surface activating molecule is a pigment molecule such as a dye particle. In a preferred embodiment the invention is used as an adhesive to bind a pigmented hydrophilic layer to a more hydrophobic article or layer. The pigmented hydrophilic layer is preferentially composed of latex, nylon, aminopolystyrene, or any other nucleophilic top coating.

This disclosure will enable those skilled in the art to grasp the potential of these novel heterobifunctional agents to produce a variety of immobilzed products. Examples herein described are meant to be illustrative only and not limitive on the scope of the invention.

The following reagents were used in the course of developing this invention. Sources are given where relevant, otherwise they are of the standard commercial grades available.

Phosphate Buffered Saline (PBS): 0.1M, pH 7.2. Available from Sigma Chemical, St. Louis Mo.

PBS-Tween: PBS solution with 0.1% tween detergent.

Carbonate buffer: 0.05M Solution. Available from Sigma Chemical, St. Louis Mo.

Non-specific blocking solution (NSB Solution): Bovine serum albumin (Intergen, Purchase NY), 1 g, with 0.5 g trehalose added to 200 mls phosphate bufer.

Enzyme conjugate solution: Goat anti-rabbit IgG conjugated to horseradish peroxidase. Available from Sigma Chemical, St. Louis Mo., diluted in NSB solution.

Enzyme Substrate: Tetramethyl benzidine (TMB) solution was obtained from Kiregaard and Perry, Gaithersberg, Md.

EXAMPLE 1

Figure 3:
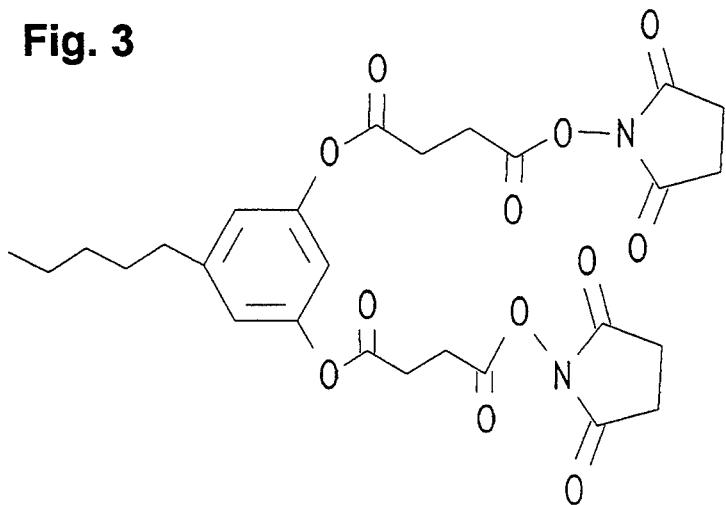
FIG. 3 shows the structure of the heterobifunctional crosslinker developed using dihydoxy pentyl benzene as a starting material.
Figure 4:
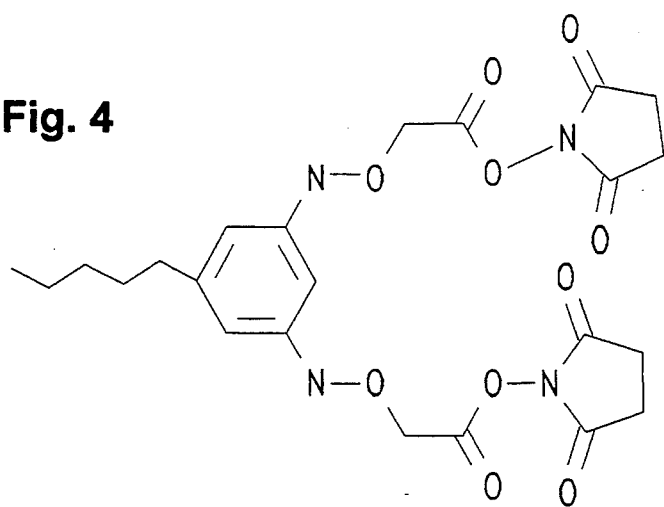
FIG. 4 shows the structure of the heterobifunctional crosslinker developed using dioximino pentyl benzene as a starting material.
Figure 5:
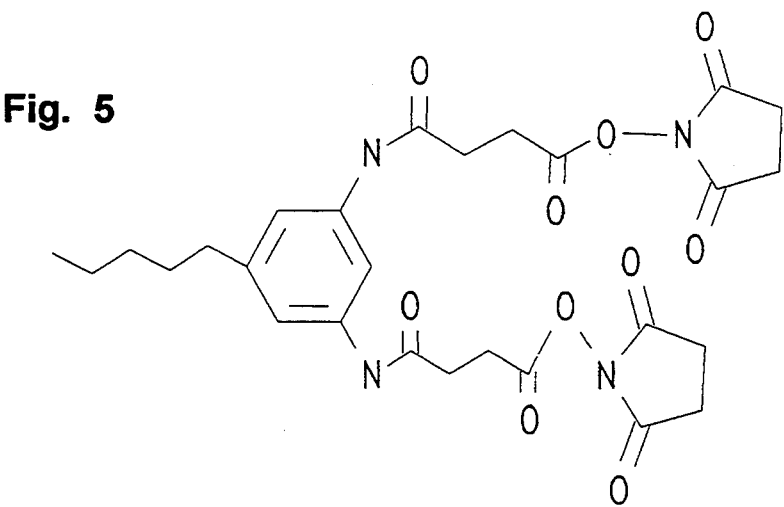
FIG. 5 shows the structure of the heterobifunctional crosslinker developed using diamino pentyl benzene as a starting material.

Synthesis of succinyl-olivetol-N-hydroxy succinimde (SON) compound shown in FIG. 3 was accomplished as follows. All materials and solvents were obtained from Aldrich Chemicals (Milwaukee, Wisc.). 0.1 g of pentyl resorcinol was dissolved in 2 mls dioxane. In a separate container anhydrous succinic anhydride in excess of two moles w/w was dissolved in two mls dioxane. Both solutions were added to a sealed glass vessel under nitrogen and sonicated for 60 minutes in a 45 watt sonicating bath, followed by 6 hours at 60 degrees centigrade. The solvent was removed under a nitrogen stream and the brown oil thus obtained was resuspended in dichloromethane. The solution was washed with two volumes of water, and the organic phase was dried with molecular sieve and the solvent removed under a nitrogen stream. The oil was resuspended in dixoane and N-hydroxysuccinimide equivalent to two moles w/w were added. The final compound was obtained by adding the condensing agent dicyclocarbodiimide. The crystals of dicyclourea were removed by filtration and the resulting SON purified by standard chromatographic means. The usefullness of this compound is demonstrated by the following examples.

EXAMPLE 2

Comparison of antibody binding on Immulon I coated with SON.

Immulon I microtiter plates (Dynatech) were coated with SON, prepared as in example 1, diluted 1/150 in methanol or were uncoated blanks. Rabbit anit-sulfamethazine antibody was added to each well and incubated one hour at room temperature. Wells were washed three times with PBS-tween and nonspecific reactions blocked with BSA-Trehalose. Anti rabbit enzyme conjugate was added to each well and incubated one half hour at room temperature. Wells were washed three times with PBS-tween and TMB substrate added to each well. SON greatly increased binding of anti-sulfamethazine on Immulon I plates (Table 1).

TABLE 1

| Elisa Comparisons of antibody attachment with and without SON. ||
| SON | Blank |
| --- | --- |
| 0.534 | 0.169 |
| 0.513 | 0.166 |
| 0.586 | 0.167 |

EXAMPLE 3

Succinyl-olivetol-N-hydroxy succinimide prepared as describe in Example 1 is used to produce plastic articles other than microtiter plates. SON dissolved to a concentration of 2 mg/ml in methanol and added to a 0.1 gram of polyethylvinyl acetate beads, 10 micron average diameter (Polysciences, Warrington, Pa.). After evaporation of the solvent under a nitrogen stream the beads are capable of iramobilizing protein reagents.

EXAMPLE 4

Using pently resorcinol as a starting material a second derivative is made. Pentyl resorcinol is dissolved in dioxane. Two moles of glutaric anhydride are added and reacted at temperatures and conditions sufficient to produce the ester. The free carboxylic acid groups on glutarate are converted to the corresponding acid chlorides through the action of thionyl chloride. The reagent thus obtained has the ability to crosslink amines, imines, and hydroxylated compounds to plastic surfaces under both aqueous and organic conditions.

EXAMPLE 5

Figure 2:
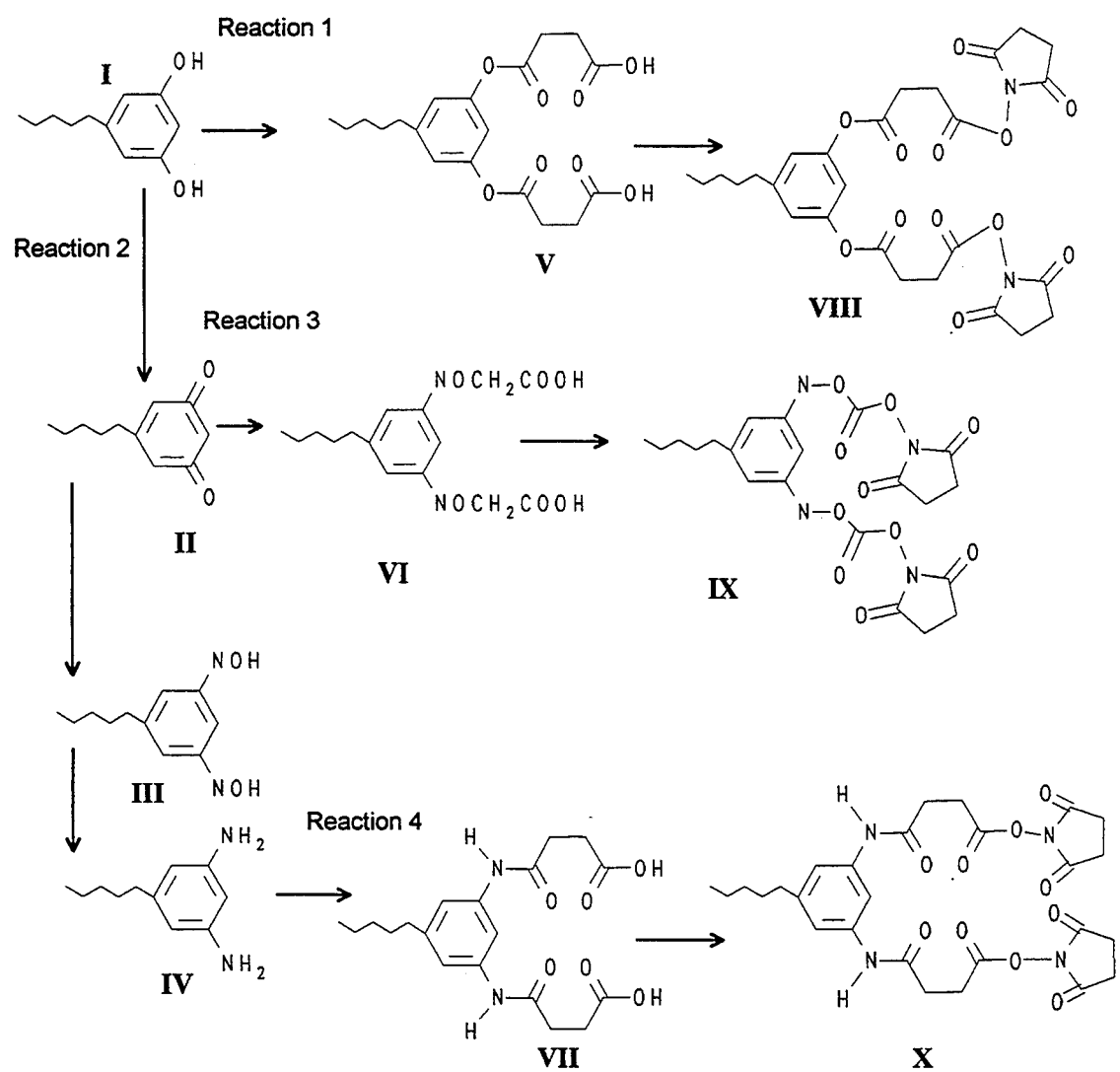
FIG. 2 shows the steps needed for synthesis of three different compounds having rapid surface activating properties.

FIG. 2 shows a reaction scheme used to generate novel compounds with heterobifunctional crosslinking capabilities. The production of succinyl-olivetol-N-hydroxy succinimide as discussed in Example 1 is shown for comparison.

Reaction 1: Compound I (Olivetol) was treated with an excess of succinic anhydride to produce Compound V. Subsequent esterification of V with N-Hydroxysuccinimide in the presence of Dicyclocarbodiimide produced the heterobifunctional agent VIII.

Reaction 2: Compound I (Olivetol) was treated with an excess of potassium permanganate oxidizer to yield Compound II (dicarbonyl pentyl benzene). Compound II was further reacted with Hydroxylamine to produce Compound III, an oxime. Subsequent reduction with hydrogen in the presence of palladium catalyst yielded Compound IV, diamino pentyl benzene. Reaction 3: The carbonyl oxygens of Compound II were reacted with carbomethoxylamine to produce Compound VI, a dioxime. The carboxylic acid moieties were subsequently esterified with N-hydroxy-succinimide to produce the heterobifunctional agent IX.

Reaction 4: The free amines of IV were reacted with an excess of succinic anhydride to produce Compound VII. Esterification with N-hydroxysuccinimide yielded the heterobifunctional agent X.

The compounds were tested by binding to plastic surfaces using solutions of 2 mg/ml in ethanol, followed by drying, and then contacting the derivatized surface with Horseradish peroxidase enzyme solution Sigma Chemical, St. Louis, Mo.) at a concentration of 10 ng/ml in carbonate buffer. After rinsing in phosphate buffered saline, enzyme binding was detected by adding TMB colofimetric substrate. Each of the compounds were tested on two different plastics, an opaque low density polystyrene and an optically transparent polycarbonate. A negative control of unmodified plastic similarly treated with enzyme was used to measure background binding.

The results of the assay are shown in Table 2.

TABLE 2

| Enzyme activity (Increase in absorbance units per minute). | | |
| --- | --- | --- |
| Compound | Polyethylene plastic | Polycarbonate plastic |
| VII | 0.11 | 0.24 |
| IX | 0.02 | 0.20 |
| X | 0 | 0.14 |
| Control | 0 | 0 |

EXAMPLE 6

The novel compound, succinyl-olivetol-N-hydroxysuccinimide (SON), was synthesized according to methods fully described in example 1. This heterobifunctional agent, identical to FIG. 3 of the specification, is capable of forming a reactive surface in a single step. In this example the plastic surface is a paddle-like "dipstick" having a wide flat reaction area (about 5 mm by 10 mm) connected by a stem of material forming a handle. The dipstick is composed of molded polystyrene. The use of a dipstick allows the rapid derivatizing aspect of the invention to be more fully illustrated.

Experimental Steps

Materials:

Tube 1 contains 1 ml of a succinyl-olivetol-N-hydroxysuccinimide (SON) solution at 0.2 mg/ml in dry ethanol.

Tube 2 contains 1 ml of dry ethanol to serve as a control test.

Tube 3 contains 1 ml of a 0.01 mg/ml of horseradish peroxidase enzyme solution in 0.05% sodium carbonate buffer. The peroxidase enzyme is a native unmodified preparation. The carbonate buffer is not a limitive condition, merely illustrative of a common laboratory solution.

Tube 4 contains a phosphate buffered rinsing solution used to dilute unbound enzyme.

Tube 5 two separate tubes containing TMB substrate (Kirkegaard and Perry, Gaithers burg, Md.) for detecting peroxidase enzyme activity. TMB turns from colorless to deep blue in the presence of peroxidase.

Reaction Series

Step 1: Plastic dipsticks are placed into tube 1 and tube 2. After 2 minutes the dipsticks are withdrawn and excess alcohol allowed to evaporate (peroxidase is an alcohol sensitive enzyme). The surface is now derivatized and will bind amine bearing compounds.

Step 2: The dipsticks are placed in tube 3 and allowed to bind the enzyme for 3 minutes. The dipsticks are removed from the solution, blotted dry, and rinsed in tube 4.

Step 3: The dipsticks are each placed into a solution of TMB enzyme substrate (tube 5). The appearance of a blue color is proportional to enzyme binding.

The compound was tested for ability to rapidly derivatize a plastic surface. A negative control of unmodified plastic, treated only with alcohol and enzyme, was used to measure background binding. The reacted TMB enzyme substrate was measured for absorbance at 620 nm using a colorimeter and the results are in Table 3.

TABLE 3

| Enzyme activity (increase in absorbance) of a 2 minute treatment. | |
| --- | --- |
| Treatment | Absorbance at 620 nm |
| Tube 1 (SON) | 0.12 |
| Tube 2 (control) | 0 |

EXAMPLE 7

In this example the plastic article is contacted with SON, the compound of example 1. The reagent layer is a solution of aminopolystyrene latex and pigments capable of bonding to immobilized SON to form an inert top coat on the article.

We claim:

1. A heterobifunctional crosslinking agent for producing an activated plastic substrate in a single, step, comprising:

the molecule of the structure:

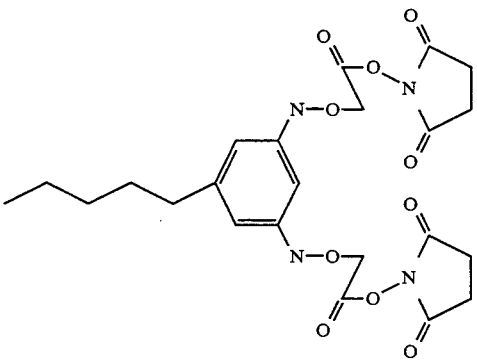

wherein said structure:

is a hydrophobic member for bonding said molecule to a plastic substrate; and said structures:

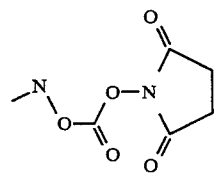

are hydrophilic joining members having terminal reactive members for binding a reagent member.

2. A heterobifunctional crosslinking agent for producing an activated plastic substrate in a single, step, comprising:

the molecule of the structure

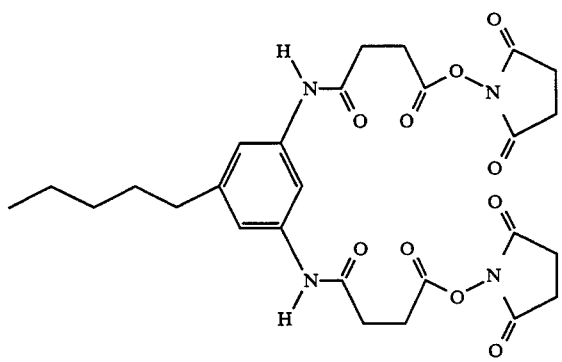

wherein said structure:

is a hydrophobic member for bonding said molecule to a plastic substrate; and said structurs:

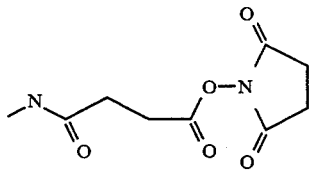

are hydrophilic joining members having terminal reactive members for binding a reagent member.

3. The heterobifunctional crosslinking agent of claim 1 or 2 wherein said agent is bound by said hydrophobic member to a plastic substrate made from a polymer selected from the group consisting of polypropylene, polyethylene, polycarbonate, polysulfone, polyvinyl, polymethacrylate, and derivatives and combinations thereof; said plastic being in the form of a sheet, cup, rod, tube, fiber, coating or bead, either porous or nonporous.

4. The heterobifunctional crosslinking agent of claim 1 or 2 wherein a reagent member is bound to said reactive members and said reagent member is selected from the group consisting of an enzyme; antibody, either monoclonal or polyclonal; amino acid; cell, either microbial, plant, or animal; drug, or drug analog; and polynucleotides, either single or double stranded DNA or RNA wherein said reagent member is useful in diagnostic assays or bioreactors.

5. The reagent member of claim 4 wherein said reagent member is an inert nucleophilic material forming a top coating.

* * * * *